United States Patent [19]

Hatschek

[11] Patent Number: 4,459,991

[45] Date of Patent: Jul. 17, 1984

[54] BLOOD PRESSURE MEASURING EQUIPMENT

[75] Inventor: Rudolf A. Hatschek, Fribourg, Switzerland

[73] Assignee: Asulab A.G., Biel, Switzerland

[21] Appl. No.: 235,564

[22] Filed: Feb. 12, 1981

[30] Foreign Application Priority Data

Feb. 18, 1980 [CH] Switzerland ............... 1296/80

[51] Int. Cl.³ .............................................. A61B 5/02
[52] U.S. Cl. ..................................... 128/681; 128/682
[58] Field of Search ................................ 128/680–683, 128/686, 677–679, 684, 685

[56] References Cited

U.S. PATENT DOCUMENTS

| | | | |
|---|---|---|---|
| 3,654,915 | 4/1972 | Sanctuary | 128/682 |
| 3,905,353 | 9/1975 | Lichowsky | 128/677 |
| 3,905,354 | 9/1975 | Lichowsky | 128/681 |
| 3,978,848 | 9/1976 | Yen et al. | 128/681 |
| 4,116,230 | 9/1978 | Govelick | 128/682 |
| 4,117,835 | 10/1978 | Williams | 128/677 |
| 4,273,136 | 6/1981 | Kubo et al. | 128/681 X |

FOREIGN PATENT DOCUMENTS 1259502 1/1968 Fed. Rep. of Germany ...... 128/677

Primary Examiner—Kyle L. Howell
Assistant Examiner—John C. Hanley
Attorney, Agent, or Firm—Michael J. Striker

[57] ABSTRACT

There is disclosed blood pressure measuring equipment comprising a sleeve with an inflatable chamber and a microphone, and an appliance connected by a line with the sleeve. The appliance comprises a pressure sensor and a differentiator connected to the sensor output. The differentiator is connected with a regulator which in operation regulates a vent valve in such a manner that the pressure in the chamber during the measurement phase, in which the systolic and diastolic pressures are measured, reduces at a constant rate. A Korotkoff tone identifier, which is connected through further elements with the microphone and the differentiator, ensures that only those signals from the microphone which occur simultaneously with a heartbeat-induced pressure fluctuation are delivered as Korotkoff tones and evaluated for determination of the systolic and diastolic pressure.

10 Claims, 5 Drawing Figures

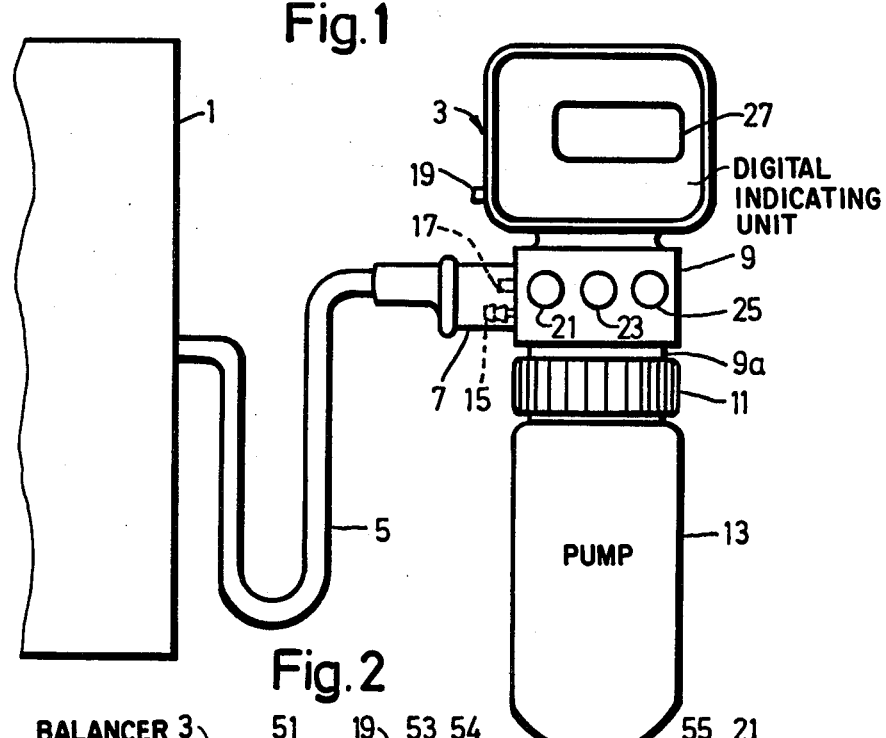
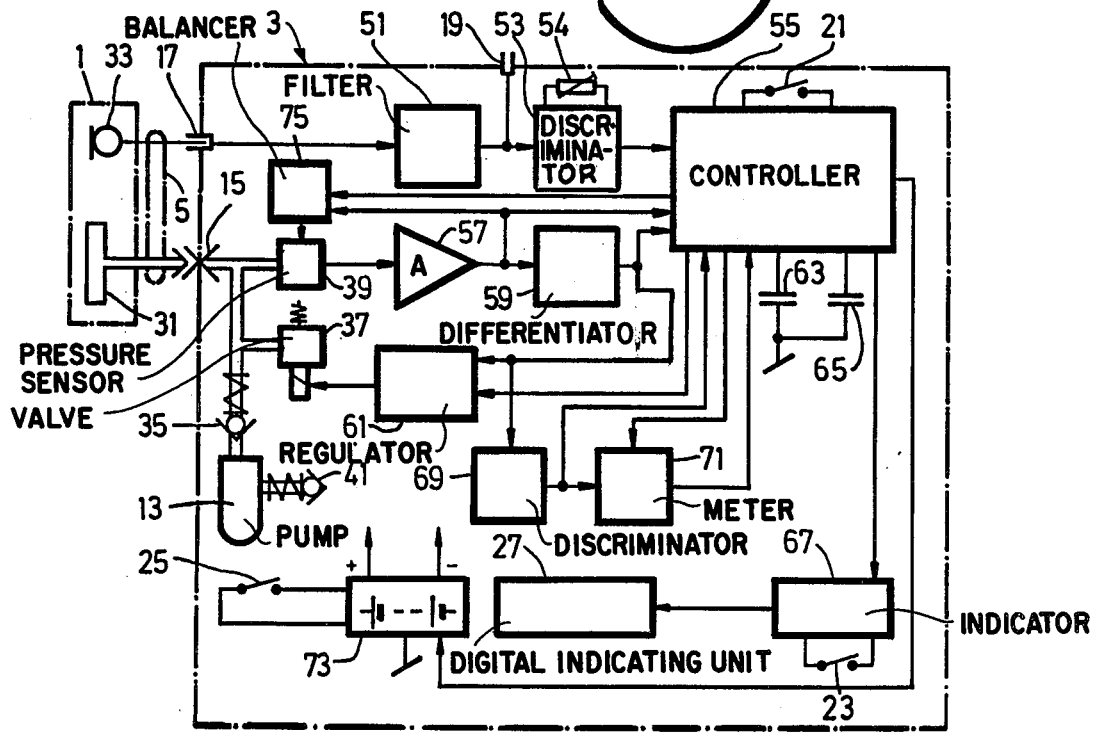

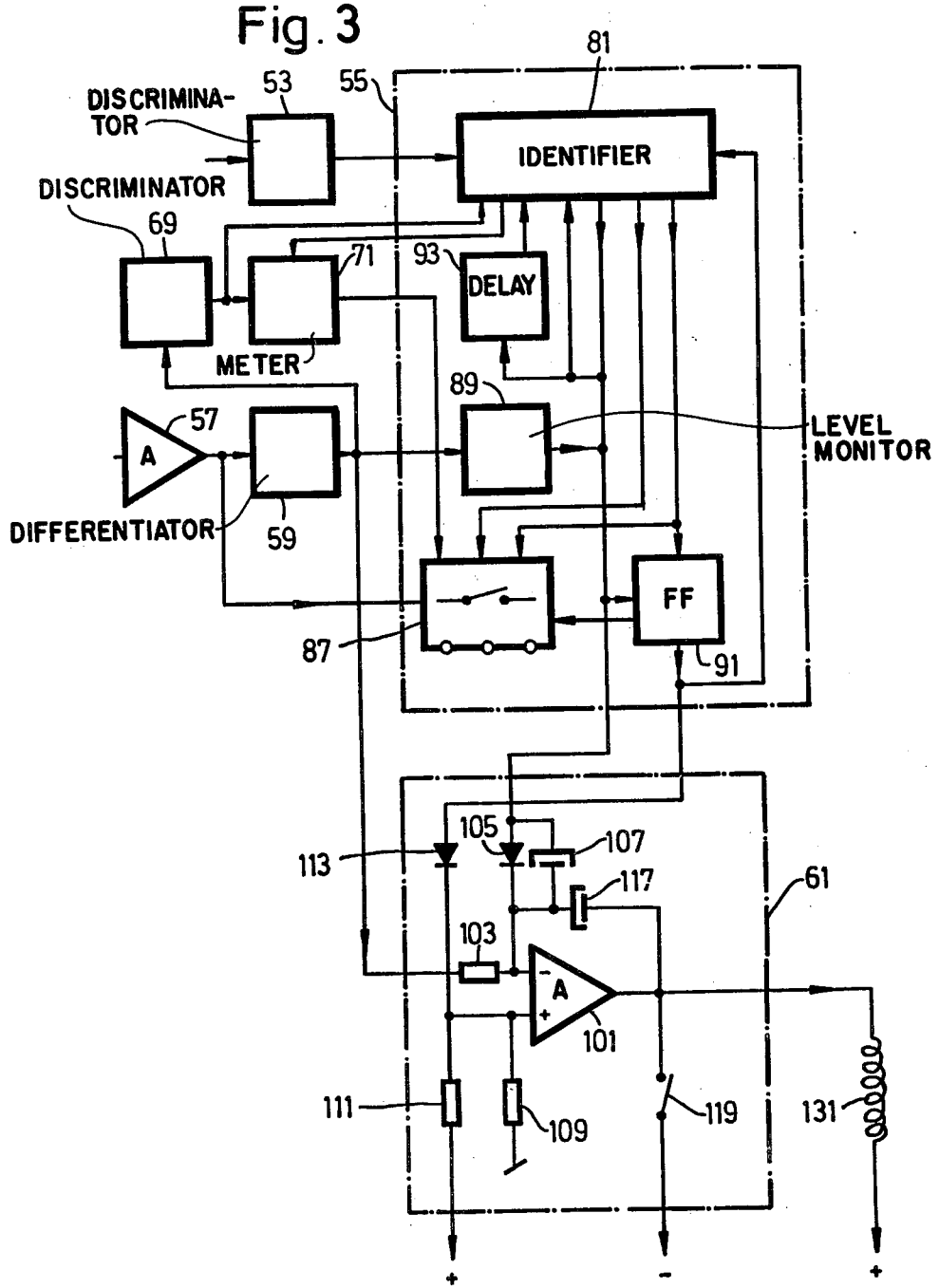

BLOOD PRESSURE MEASURING EQUIPMENT

BACKGROUND OF THE INVENTION

The present invention relates to a blood pressure measuring equipment more particularly to a sphygmometer.

Blood pressure measuring equipment described in U.S. Pat. No. 2,827,040 comprises a microphone for detection of the Korotkoff tones generated by blood flowing through an artery. The microphone is connected via an amplifier, a bandpass filter and a pulse shaper with a coincidence circuit. An inflatable sleeve, which is attachable to the arm of the person to be examined, is connected with an air reservoir having an outlet nozzle which, during measurement, generates an air jet flowing past a thermistor. The thermistor, which serves for detection of pressure pulses, is similarly connected via an amplifier and a pulse shaper with the coincidence circuit. In addition, a manometer for detection of systolic pressure and a manometer for detection of diastolic pressure are provided. Each of the manometers is connected by way of a respective valve with the air reservoir. The air reservoir is connected by way of a valve with a compressor and additionally via a venting valve with the ambient atmosphere. Control equipment for actuation of the different valves is also included.

During blood pressure measurement, the pressure in the air reservoir is progressively increased. Pulses are then generated in certain pressure ranges by Korotkoff tones and by pressure fluctuations and these pulses are fed to the coincidence circuit. On the first instance of coincidence of pulses from the two sources, i.e. the coincidence occurring at the lowest pressure, the manometer for measurement of diastolic pressure is temporarily connected with the air reservoir so that it measures and indicates the diastolic pressure. Thereafter, the pressure is further increased. When the pulse coincidence at the highest pressure occurs, the manometer serving for measurement of systolic pressure is temporarily connected with the air reservoir and the systolic pressure is then measured.

This prior art equipment has the disadvantage that its appliance part connected to the sleeve must include an air reservoir and four valves, which make it correspondingly large and awkward and difficult to use as a manual appliance for single-handed operation by a physician or other person. A further disadvantage is that detection of pressure fluctuations by means of a thermistor cooled by an air current is both delicate and subject to inaccuracies.

Moreover, the temporal course of measurement in this automatic appliance is significantly different from the measurement procedure usually followed by physicians when determining blood pressure by conventional manual appliances. With these appliances, a measuring sleeve is initially rapidly pumped up to a pressure above systolic pressure. Thereafter, the sleeve is slowly vented while the onset and conclusion of the production of Korotkoff tones is determined with the aid of a stethoscope. The duration of the pressurisation of the sleeve and the temporal course of the pressure can, however, influence the measurement results. An automatic appliance in which the temporal pressure course is substantially different from the above-described traditional measurement process carried out by physicians can give rise to measurement errors or, at the least, render more difficult a comparison of measurement results obtained by the automatic appliance with those obtained by a traditional method.

Another blood pressure measuring equipment described in U.S. Pat. No. 3,450,131 comprises a microphone which is connected via a regulated amplifier and bandpass filter with a logic circuit. The equipment also includes an inflatable sleeve and a pressure sensor which is connected through a switchable analog-digital converter and a gate circuit with a pressure recording appliance.

For blood pressure measurement, the sleeve is inflated to a pressure above systolic pressure and then slowly vented. Korotkoff tones are then generated in a certain pressure range and are converted by the microphone into electrical signals. The logic circuit connected to the output of the filter operates in such a manner that it can identify signals with a 1000 Hertz component as noise signals, and signals with a 40 and a 100 Hertz component, but no 1000 Hertz component, as Korotkoff tones. On each identification of a signal as a Korotkoff tone, the analog-digital converter and the gate circuit are controlled by the logic circuit in such a manner as to cause the instantaneous pressure measured by the pressure sensor to be recorded in the pressure recording appliance. The first recorded pressure value then corresponds to systolic pressure and the last recorded pressure value to diastolic pressures. There is also the possibility of providing an additional circuit which records only the systolic and diastolic pressures.

In the equipment described in U.S. Pat. No. 3,450,131 the Korotkoff tones are thus identified exclusively on the basis of their frequencies and differentiated from interference noises. However, as Korotkoff tones are very soft in the region of the diastolic pressure, identification of Korotkoff tones in this manner is susceptible to error.

The sleeve of this equipment is inflated and vented under the control of control unit which is not described in detail. As there is no electrical connection between this control unit and the pressure sensor, it evidently operates independently of the pressure measurement. It is therefore to be assumed that during the venting phase, the air flows, independently of the instantaneous pressure, through an outlet which includes a valve and possibly also a throttle and which has a constant flow cross-section during the entire venting phase. However, this has the consequence that the outflow speed at the start of the venting phase, when the pressure is high, is greater than towards the end of the venting phase. As a result, the pressure reduction per unit in time is greater during measurement of systolic pressure than during measurement of diastolic pressure. This in turn has the consequence that systolic pressure is measured with less accuracy than diastolic pressure. If, on the other hand, the temporal pressure reduction is set to take place at such a slow rate that a certain minimum level of measurement accuracy is achieved during measurement of systolic pressure, the measurement of both pressures occupies a relatively long period of time. This is particularly so because the outflow speed becomes even smaller below the diastolic pressure, so that complete venting of the sleeve can take a very long time. A further disadvantage of this equipment is that there is an appreciable risk of under-inflation of the sleeve, so that the pressure measured on arrival of the first Korotkoff tone and regarded as systolic pressure in fact lies below the true systolic pressure.

For the sake of completeness, it is mentioned that U.S. Pat. Nos. 3,903,872, 4,078,551, 4,137,907, 4,140,110 and 4,144,879 also disclose pressure measuring equipment in which electrical signals dependent on pressure are formed by a pressure sensor and further signals are formed from these by differentiation, blood pressure values then being determined from the different signals. In these known items of equipment, however, microphones are not used so that it is not possible to utilise Korotkoff tones for detection of systolic and diastolic pressures. Such items of equipment therefore operate in a manner substantially different from that of the previously described known equipment and in general are very complicated and presumably correspondingly susceptible to errors and faults.

OBJECTS OF THE INVENTION

The present invention has as its primary object the provision of blood pressure measuring equipment which avoids the disadvantage of the recited prior art equipment and by means of which it may be possible to measure both systolic and diastolic pressure with a high level of accuracy and in a relatively short measuring time.

A subsidiary object of the invention is the provision of equipment of the kind described in which pneumatic and electronic components required for measurement and control require relatively little space and can be accommodated in a handy appliance capable of being held and operated by one hand during measurement.

Yet another object of the invention is the provision of blood pressure measuring equipment whereby signals generated by Korotkoff tones can be identified with the greatest possible certainty and distinguished from interference signals.

Other objects and advantages of the invention will be apparent from the following description.

SUMMARY OF THE INVENTION

According to the present invention there is provided blood pressure measuring equipment comprising measuring means attachable to a person, the measuring means comprising a microphone for detection of blood flow generated Korotkoff tones, and means, for example an inflatable sleeve worn as an armband, defining a chamber deformable by a fluid, preferably air. A pump is provided for pumping fluid into the chamber for deformation thereof and also a valve for controlling fluid outflow from the chamber. Fluid pressure in the chamber is detected by a pressure sensor which generates an electrical signal indicative of detected pressure, and a differentiator is electrically connected to the sensor to provide an electrical signal indicative of the rate change in said pressure.

For clarification, it is noted that the references in the following description and claims to blood pressure and air chamber pressure are to be understood as denoting excess pressure measured with respect to ambient air pressure.

BRIEF DESCRIPTION OF THE DRAWINGS

An embodiment of the present invention will now be more particularly described by way of example and with reference to the accompanying drawings, in which:

FIG. 1 is a schematic plan view of blood pressure measuring equipment according to the said embodiment, FIG. 2 is a schematic block diagram of the principal electronic and pneumatic components of the equipment of FIG. 1, FIG. 3 is a circuit diagram of a control unit and a regulator of the equipment.

DESCRIPTION OF THE PREFERRED EMBODIMENT

Figure 4:
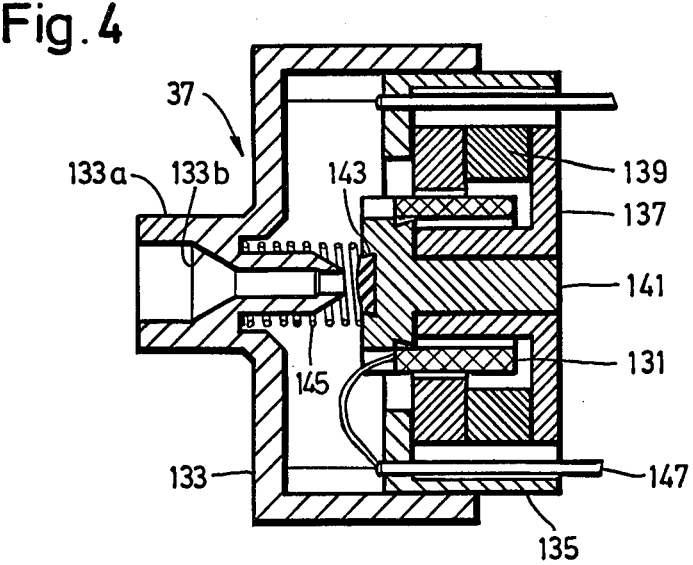
FIG. 4 is a cross-section, to an enlarged scale, of an outflow valve of the equipment.

Referring now to the accompanying drawings, in FIG. 1 there is shown blood pressure measuring equipment comprising a sleeve or cuff 1 attachable to the arm of a person to be examined and an appliance indicated generally by 3. The sleeve 1 comprises a rubber bag defining a deformable and inflatable air chamber and contains a microphone. The sleeve 1 is detachably connected to the appliance 3 by a line 5, which comprises an air hose connected to the air chamber and a cable connected to the microphone, the line being provided at the appliance end with a coupling socket 7. The appliance 3 comprises a housing 9 provided with a threaded shank 9a to which a pump 13 with a substantially cylindrical rubber pump bulb is detachably fastened by means of a box nut 11. An air hose connection nipple 15 and an electrical connection pin 17, formed by a chassis plug, are provided on the housing 9 for coupling thereto of the socket 7. A connection element 19, also formed by a chassis plug, is included for the connection of a headphone. The appliance 3 also comprises three pushbutton switches 21, 23 and 25, a digital indicating unit 27 and various pneumatic and electronic components, as will be subsequently described, accommodated in the interior of the housing 9.

FIG. 2 shows the inflatable air chamber 31, and the microphone 33, of the sleeve 1 as well as some of the pneumatic and electronic components in the appliance 3. The air chamber 31 is connected by the air hose in the line 5, and by air lines in the appliance 3, via a check valve 35 with the pump 13, an electrically controllable outflow vent valve 37 and a pressure sensor 39. The pump 13 is provided with an air inlet having a check valve 41. The two return valves 35 and 41 are so arranged that by alternating manual compression and release of the pump bellows 13 air can be sucked from the ambient atmosphere and pumped into the air chamber 31.

The microphone 33 is connected by electrical conductors with the input of a filter means 51, the output of which is connected with the headphone connection element 19 and with a discriminator 53, which comprises a trimming potentiometer 54 for setting of a lower threshold value and a pulse shaper. The output of the pulse shaper is connected to a control unit 55.

The pressure sensor 39 comprises a measurement converter bridge circuit formed by piezo-resistive elements and is connected with the input of an amplifier 57, the output of which is connected via a differentiator 59, and via a parallel connection bridging the differentiator, with the control unit 55. The control unit 55 and the amplifier 57 are also connected at outputs thereof with a device 75 for automatic zero balancing, the output of the device 75 being connected to the pressure sensor 39. The output of the differentiator 59 is also connected to the control unit 55 and additionally to an input of a regulator 61. The control unit 55 is connected to another input of the regulator 61, the output of which is connected with an electromagnetic actuating means of the outflow valve 37. The control unit 55 additionally has two connections which are connected to, respectively, two analog memories 63 and 65 each formed by a respective capacitor, and is connected to an indicating control device 67. The device 67 includes, amongst other things, an analog-digital converter and is connected to the indicating unit 27.

A discriminator 69 is connected at its input to the output of the differentiator 59, and at its output to an input of a heartbeat frequency meter 71 and an input of the control unit 55. The meter 71 is connected at a control input thereof to an output of the control part 55 and comprises an analog memory connected at an output to an input of the control unit 55. The switch 21 is connected to the control unit 55 and the switch 23 to the indicating control device 67. Also present is a voltage source 73, which includes a battery and which is connected to supply voltage connections of the different operative components and to an earth connection. The switch 25 and also the control unit 55 are connected to the voltage source 73, which, part from the battery, comprises logic elements and a regulator for stabilisation of the supply voltage. The battery is accommodated in a battery compartment closable by a lid.

Certain of the components of the control unit 55 and the connections thereof to each other and to other components of the equipment will now be explained with reference to FIG. 3.

The output of the discriminator 53 and the output of the discriminator 69 are connected with different inputs of Korotkoff tone identifier 81 of the control unit 55. The identifier 81 includes AND-gates, which are connected together and one of which serves as a coincidence circuit as will be subsequently explained, and at least one flipflop. The identifier 81 also comprises a detector which, amongst other things, serves for recognition of the last Korotkoff tone and which is composed of elements for exercise of logic functions and determination of at least one time interval. One output of the identifier 81 is connected to an electronic multiple switching device 87. Another output of the identifier 81 is connected to the control input of the heartbeat frequency meter 71. The outputs of the amplifier 57 and meter 71 are also connected to inputs of the multiple switching device 87. The switching device includes connections which are connected to components not illustrated in FIG. 3, namely the memories 63 and 65 and the indicating control device 67. The output of the differentiator 59 is connected to the input of a level monitor 89.

As will be explained, the purpose of the discriminator 69 is to provide pulses indicative of pressure fluctuations generated by heartbeats. The discriminator 69 is accordingly constructed in such a manner that it generates pulses on those pressure fluctuations at which the differential quotient dp/dt is positive and exceeds a given threshold value of at least 100 Pascals per second, for example about 300 to 400 Pascals per second.

The level monitor 89 also responds when the temporal pressure rise, i.e. the differential quotient dp/dt, exceeds a predetermined upper limit value. This limit value, however, is greater than the differential quotients arising as a consequence of the heartbeats and is at least about 2000 Pascals per second, for example 3000 to 7000 Pascals per second.

The output of the level monitor 89 is connected with an input of a flipflop 91 and with the identifier 81 both directly and via a time delay element 93. A further output of the identifier 81 is connected to another input of the flipflop 91 and also to the switching device 87. One output of the flipflop 91 is connected to the identifier 81 and another output of the flipflop to the multiple switching device 87.

The regulator 61, the circuit diagram of which is also shown in FIG. 3, comprises a differential amplifier 101 having its inverting input connected via a resistor 103 with the output of the differentiator 59. In addition, the output of the level monitor 89 and an output of the identifier 81 are connected, via a diode 105 with a parallel-connected capacitor 107, to the inverting input of the amplifier 101. The non-inverting input of the amplifier 101 is connected via a resistor 109 with ground, via a resistor 111 with the positive pole of the voltage source 73, and via a diode 113 with the output of the flipflop 91 connected to the identifier 81. The output of the amplifier 101 is connected via a capacitor 117 with the inverting input and, via a switch 119, with the voltage source 73. The switch 119 is arranged in the interior of the battery compartment, which must be opened if it is intended to actuate the switch 119. The output of the amplifier 101 is also connected with one terminal of a coil 131 of the outflow valve 37, the other terminal of which is connected to the positive pole of the voltage source 73.

The electronic components illustrated in FIGS. 2 and 3 can be constructed as integrated circuits.

As shown in FIG. 4, the outflow valve 37 comprises a housing with two parts 133 and 135. The housing part 133 is provided at the centre of its outer end face with a connection 133a having an inlet passage 133b. The connection 133a has an extension projecting into the interior of the housing and is connected by way of the lines shown in FIG. 2 with the air chamber 31 and with the other previously described components. The interior space of the housing is in communication through at least one outlet passage (not shown) with the environment. A yoke 137 with a ferromagnetic ring 139 is fastened to the housing part 135. Arranged to be axially displaceable in a hollow cylindrical portion of the yoke 137 is an armature 141, to which the coil 131 is fastened. The armature 141 is provided with a rubber sealing member 143 at its end facing the outlet end of the inlet passage 133b. A compression spring 145 presses the armature 41 away from the outlet end of the inlet opening 133b. The coil 131 is connected by way of a cable 147 with the output of the amplifier 101 and with the positive pole of the voltage source 73.

When the coil 131 is free of current, the armature 141 is disposed in the illustrated opening setting in which air under pressure, fed through the inlet passage 133b, can flow into the interior of the housing and out through the oulet passage or passages into the environment. When a voltage is applied to the coil 131, the armature 141 is displaced towards the outlet end of the inlet passage 133b to reduce the flow cross-section of the valve in correspondence with the magnitude of the applied voltage or to close the valve entirely.

The operation of the blood pressure measuring equipment will now be explained in detail with reference to FIG. 5.

For performance of a measurement, the sleeve 1 is connected by the line 5 with the appliance 3 and is attached to the arm of the person to be examined. The dimensions of the appliance 3 are such that it can conveniently be held by one hand, for which purpose the pump 13 also serves as a handgrip. When necessary, all three pushbutton switches 21, 23 and 25 can be actuated by the hand holding the appliance.

To begin with, the change in pressure p in the air chamber 31 in relation to the course of time t will be discussed. The temporal course of the pressure p is represented by the curve 151 of the diagram illustrated in FIG. 5. The pressure sensor 39 during measurement generates a voltage which is proportional to the pressure p.

When the sleeve is attached, the appliance is made operationally ready at the instant $t_0$ through a brief depression of the ON/OFF switch 25. The valve 37 is fully open at this instant and in the time interval from the instant $t_0$ to the instant $t_1$, whereupon it automatically closes. During this time interval, the pressure sensor 39 is automatically balanced to zero by the zero balance device 75. The end of this balance at the instant $t_1$ is signalled by the indicating unit 27 indicating the value zero.

Air is now pumped into the air chamber 31 by means of manual actuation of the pump 13. As a result, the pressure in the chamber 31 rises in steps so that the differential quotient dp/dt has a relatively high positive value which exceeds the limit value monitored by the level monitor 89. The level monitor 89 and generally exceeding any rate of change on pressure in the cuff 1 that could be created by the blood pressure of the limb to which this cuff is attached therefore feeds to the inverting input of the amplifier 101 a voltage which has the effect of causing the regulator 61 to completely close the valve 37. This state of affairs is illustrated by the curve 153 of FIG. 5, which represents the temporal course of the flow cross-sectional area q of the valve 37.

During the inflation process, the pressure in the chamber 31 is continuously indicated by the indicating unit 27 and the feed of measurement values through the switching device 87 is controlled in such a manner that the values are indicated at constant time intervals of, for example 0.3 seconds. When the pressure has risen to a level sufficiently above the expected systolic pressure $p_S$, the inflation process is terminated at the instant $t_2$.

The regulator 61 is constructed as integral regulator and the capacitors 107 and 117 are so dimensioned that the valve 37 remains closed after the last pump stroke for a defined time of at least one second, for example two to three seconds. At the instant $t_3$, the regulator 61 starts to open the valve 37 so that air can flow out of the air chamber 31. During this regulating stage, the regulator 61 compares the voltage fed it from the differentiator 59 with the reference voltage formed by the stabilized, positive supply voltage of the voltage divider consisting of the resistors 109 and 111. The resistors 109 and 111 are such that the mean air pressure reduces at a constant rate of about 300 to 500 Pascals per second.

With regard to the significance of the expression "mean pressure", when the pressure in the chamber 31 lies within a certain range, heart activity has the consequence, as already briefly mentioned, that a small pressure fluctuation occurs with each heartbeat. As will be explained, these pressure fluctuations are required for the measurement and should not be eliminated by the regulation or, at most, reduced by anything more than a small amount. The regulator 61 is accordingly constructed in such a manner that the regulating time constant of the entire regulating circuit, to which the amplifier 57, the differentiator 59 and the valve 37 also contribute, is at least 0.15 seconds. However, in order for the temporal decrease of the mean pressure to be regulated to a substantially constant value during the measurement time interval of interest, the regulating time constant is preferably at most 2 seconds, for example about 0.5 seconds.

When the pressure p is now reduced from its maximum lying above the systolic pressure $p_S$, the pressure fluctuations caused by heartbeats occur from the instant $t_4$. These pressure fluctuations are detected by the differentiator 59 and converted into corresponding signals. The discriminator 69 then generates a pulse which is fed to the coincidence circuit of the identifier 81 on each pressure fluctuation generated by a heartbeat. These pulses form a pulse sequence which is designated by 155 in FIG. 5.

When the pressure in the air chamber 31 is reduced to be in a certain range, blood flowing through the artery enclosed by the sleeve 1 generates noises, the so-called Korotkoff tones, on each blood stroke generated by a heartbeat. These Korotkoff tones are converted by the microphone 33 into electrical signals and transmitted through the filter means 51, which preferably also amplifies the signals, to the discriminator 53. When the voltage of the Korotkoff tone signals exceeds the lower threshold value determined by the discriminator 53, the pulse shaper of the dirciminator 53 feeds a respective pulse to the identifier 81 of the control unit 55. This pulse sequence is designated by 157 in FIG. 5 and extends from the instant $t_5$ to the instant $t_6$.

Figure 5:
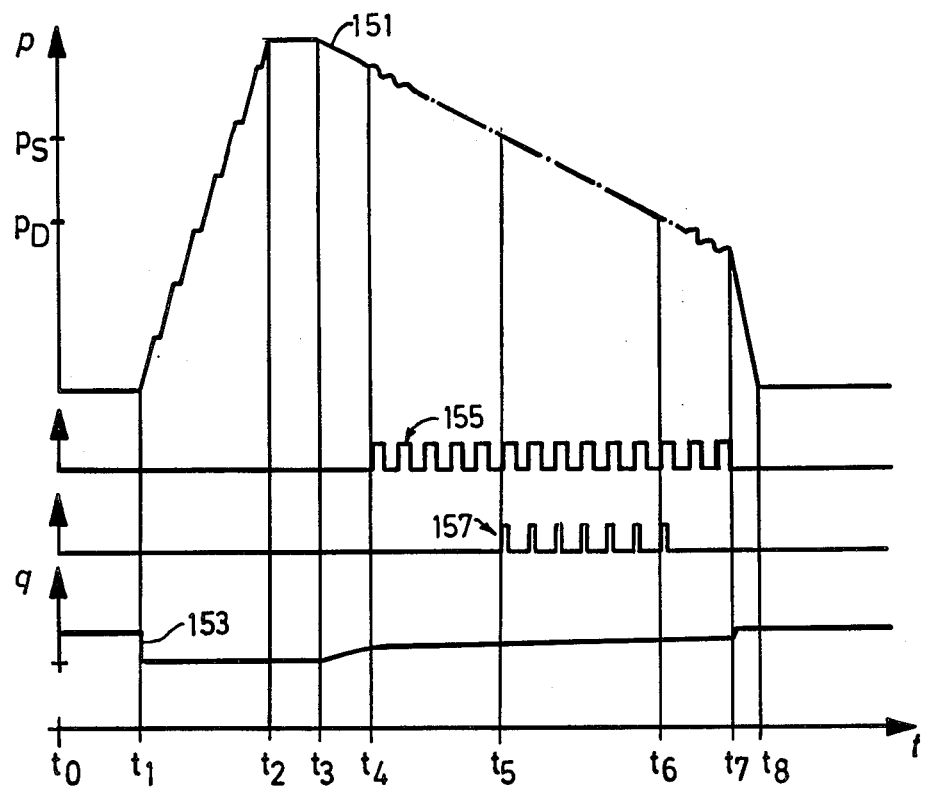
FIG. 5 is a diagram illustrating the temporal course of a blood pressure measurement by the equipment.

As is evident from FIG. 5, the pulses generated through the pressure fluctuations are wider than the pulses generated through the Korotkoff tones. The widths of the pulses of the pulse sequences 155 and 157 are dimensioned in such a manner that the pulses are still superimposed when the rising edges of the pressure fluctuations and of the tones are somewhat displaced in time relative to each other. The Korotkoff tone identifier 81 opens a window for the pulses of the pulse sequence 157 during each pulse of the pulse sequence 155. Signals from the microphone are thus further processed when they fall into a window opened by a pressure fluctuation, i.e. when a coincidence exists between the tone signals and the pressure fluctuations. As a result, the Korotkoff tones can be identified as well as distinguished from interference noises and the latter can be suppressed.

It is to be mentioned that the coincidence circuit in the identifier 81 is blocked for the Korotkoff tone signals during the inflation process by the signal fed to the identifier from the level monitor 89. The time delay element 93 in that case has the effect that the Korotkoff tone signals are still blocked for a time duration of 2 to 3 seconds even after the end of the rapid pressure rise, i.e. after the termination of the inflation process.

The electronic multiple switching device 87 connects the output of the amplifier 57 from the instant $t_0$, or at least from the instant $t_4$, with the memory 63 so that the instantaneous pressure is thus at first stored continuously in the memory 63. When the coincidence circuit of the identifier 81 identifies a signal from the microphone as the first Korotkoff tone in the manner previously described, a flipflop of the identifier feeds a corresponding control signal to the switching device 87. The switching device 87 at first provisionally separates the memory 63 from the amplifier 57. The instantaneous pressure present on the arrival of the first signal identified as a Korotkoff tone is therefore provisonally stored in the memory 63 and provisionally identified as systolic pressure.

The detector also present in the identifier 81 checks whether a second pulse coincidence follows the first provisionally identified Korotkoff tone within a predetermined time interval of at least 2 seconds and at most 10 seconds, for example 5 seconds. Only if this is the case are both pulse coincidences identified as genuine Korotkoff tones. When two genuine Korotkoff tones are thus identified within the predetermined time interval, the memory 63 for the blood pressure measurement process concerned is finally separated from the amplifier 57 and the pressure stored on the first Korotkoff tone is stored as systolic pressure.

If, on the other hand, the identifier 81 does not identify a second Korotkoff tone within the predetermined time interval, the pulse coincidence provisionally identified as a Korotkoff tone is now identified as interference. The memory 63 is then again connected with the amplifier 57 until the next coincidence occurs.

As the pressure in the air chamber 31 drops, further Korotkoff tones follow the first Korotkoff tone. The identifier 81 first checks on whether each pulse from the discriminator 53 of the sound recording channel is coincident with a pulse from the discriminator 69 of the pressure measuring channel. The identifier 81 also checks whether coincidences follow one another within the predetermined time interval of 2 to 10, for example, 5 seconds. As long as this is the case, the switching device 87 briefly connects the output of the amplifier 57 with the memory 65 on each Korotkoff tone, i.e. on each pulse of the pulse sequence 157. A new pressure value is thus stored in the memory 65 on each Korotkoff tone, these pressure values progressively reducing. As already mentioned, the pulse sequence 157 extends to the instant $t_6$. As no further pulses occur after the instant $t_6$, the value of the pressure p measured at the instant $t_6$ remains stored in the store 65 until the appliance is switched off. This storage value therefore represents the diastolic pressure.

When the detector of the identifier 81 ascertains that no further Korotkoff tone has occurred during the above-mentioned predetermined time interval of 2 to 10 seconds, it feeds a corresponding signal at the instant $t_7$ to the switching device 87 and the flipflop 91. As a result, the measuring of pressure is terminated. In addition, the flipflop 91 now feeds a voltage, which is substantially greater than the previously supplied reference voltage, to the non-inverting input of the amplifier 101. This has the effect of causing the regulator 61 to fully open the valve 37. The pressure p then drops very rapidly and at the instant $t_8$ is again at the value zero, i.e. the ambient air pressure.

The measurement phase is thus terminated only when no further Korotkoff tone occurs during the time interval of 2 to 10 seconds. By this means it is ensured that the measurement is not terminated during an auscultatory gap, i.e. on the absence of the Korotkoff tones during one or possibly several heartbeats, before the pressure in the air chamber has dropped to the real diastolic pressure.

The control unit 55 is so constructed that is connects the output of the amplifier 57 with the indicating control device 67 at regular time intervals of, for example, 0.3 seconds from the zero balance up to the instant $t_8$. The indicating unit 27 then indicates the instantaneous pressure each time. The control unit 55 could, however, also be constructed in such a manner that the pressure would be indicated on each pulse of the pulse sequence 155 in the time interval between the instants $t_4$ and $t_7$.

During the time between the instants $t_3$ and $t_6$ or $t_7$ the identifier 81 also switches on the heartbeat frequency meter 71 so that this measures the heartbeat frequency during the occurrence of the pulse sequence 155 and averages it over a few pulses. The mean value is stored in the store of the meter 71.

The nature of the control 55 is such that the memory 63, the memory 65 or the memory of the meter 71 can be cyclically interrogated by a brief depression of the switch 21. The relevant storage value stored in analog form is then fed to the indicating control device 67 and converted by this into a digital signal. This is fed to the indicating unit 27 so that the unit thus selectably indicates systolic or diastolic pressure or heartbeat frequency. In addition, the indicating unit 27 indicates by a symbol which of the three measurement values is just being displayed.

The indicating control device 67 includes a network which can be switched over by the switch 23 and connected between the feed lines of the memories 63 and 65 and the analog-digital converters. This makes possible selectable presentation of the pressure indication in kilopascals or torrs, the switching between these alternative forms of indication being effected by a brief depression of the switch 23.

When all three storage values have been read off, the appliance 3 can be switched off by depressing the ON/OFF switch 25, whereby the measurement is concluded.

Now that the general mode of operation of the equipment has now been explained, a further function of the level monitor 89 will be described. As already mentioned, the level monitor 89 responds when the differential quotient dp/dt exceeds an upper limit value. Such excessively rapid pressure changes can occur not only during the inflation phase, but also when the examined person perhaps moves the arm to which the sleeve 1 is attached. When such a movement takes place between the instants $t_3$ and $t_7$, it could cause a measurement error. However, measurement errors of that kind can be prevented by means of the level monitor 89 and associated elements. When the differential quotient dp/dt exceeds the predetermined limit value as the result of an arm movement, for example at a time between the instants $t_5$ and $t_6$, this has the effect that an AND-gate of the identifier 81 is blocked for the Korotkoff tone signals and the valve 37 is closed. The time delay element 93 in that case has the effect that the Korotkoff tone signals remain blocked for a time duration of 2 to 3 seconds even after the end of the rapid pressure change, in analogous manner to the blocking at the end of the inflation process.

As already explained, the valve is opened again only after a certain temporal delay. Thereafter, the measurement proceeds normally.

The identifier 81 is also constructed in such a manner that the onward transmission of the Korotkoff tone signals is blocked when a certain minimum time interval does not elapse between the termination of the inflation process, which is ascertained by the level monitor 89, and the occurrence of the first Korotkoff tone. This minimum time interval is, for example, 2 to 5 seconds. When a Korotkoff tone signal occurs within this time interval, the transmission of this signal is prevented by the identifier 81 and the valve 37 is closed again. In addition, by means of a connection (not shown) a disturbance can be indicated by a luminescent diode (not shown) or in other manner. The person operating the blood pressure measuring equipment can further actuate the pump 13 to increase the pressure in the chamber 31. In this manner it can be avoided that too small a systolic pressure is measured due to insufficient inflation.

The blood pressure measuring equipment hereinbefore described is suitable for, inter alia, patients who measure their blood pressure themselves and from time to time communicate their measurement results to the physician treating them. The physician can on this occasion also perform measurements with the equipment. In addition, he or she has the option of listening to the Korotkoff tones by a stethoscope or a headphone connected to the connection 19 and to continuously read off the instantaneous pressure. In this manner, the physician can recognise any anomalies.

As described above, the pressure sensor 39 and the amplifier 57 are connected with the device 75 for automatic zero balancing. The amplifier 57 is also still provided with a test device, which comprises a test switch arranged in the battery compartment so that it is actuable only when the compartment is opened. Through actuation of the test switch, the bridge circuit contained in the pressure sensor 39 can be detuned in a defined manner. With the sleeve 1 separated from the appliance, a certain calibration value can then be indicated.

It is also possible to check and caibrate the entire pressure range. For this purpose, the switch 119 arranged in the interior of the battery compartment can be closed, whereby the valve 37 is fully closed. An external pressure measuring appliance can then be connected in place of the air chamber or additionally thereto and the entire pressure range checked. If so desired, recalibration can be undertaken by a trimming potentiometer associated with the amplifier 57.

The equipment can be modified in a number of ways. For example, the pressure sensor could be connected in terms of fluid with the air chamber not through lines but through direct incorporation in the air chamber.

In addition, the identifier 81, as well as the level monitor 89 and the flipflop 91, instead of acting through the regulator 61 on the valve 37 could be connected through parallel connections, which bridge over the regulator, with the coil of the valve or with control connections of controllable electronic switching means through which the coil can be switched on and off.

Moreover, to reduce the measuring time, the control unit 55 could be constructed so that although the pressure in the temporal region between the first and last Korotkoff tones reduces at a constant speed of, for example, 400 Pascals per second, the valve is opened to a greater extent in the interval between these tones, so that the pressure reduction takes place more rapidly during this interval.

Furthermore, a low pass filter could be included in the pressure measuring channel between the amplifier 57 and the indicating control device 67 and/or the memories 63 and 65. As a result, pressure fluctuations occurring on the heartbeats could, amongst other things, be filtered out.

Finally, reference is made to the specifications of Swiss patent applications Nos. 1297/80, 1298/80 and 1299/80 of the applicant, and corresponding U.S. patent application Ser. Nos. 235,561 and 235,563, in which further details of such blood pressure measuring equipment are described.

I claim:

1. Blood pressure measuring equipment comprising
   measuring means attachable to a person, said measuring means comprising
      a microphone for detection of blood flow generated tones, and
      means defining a chamber deformable by a fluid,
   pump means for pumping fluid into said chamber for deformation thereof,
   valve means for controlling fluid outflow from said chamber,
   a pressure sensor responsive to fluid pressure in said chamber to generate an electrical signal indicative of said pressure,
   differentiating means electrically connected to said sensor to provide an electrical signal indicative of the rate of change in said pressure; and
   means responsive to said rate indicative signal for causing said valve means to close when said rate indicative signal represents an increase in the pressure at least during pumping of fluid into said chamber at a rate above a predetermined upper value exceeding a value normally creatable by the blood pressure of a person to which the cuff is attached.

2. Equipment according to claim 1, comprising regulating means controllable by said differentiating means to so regulate said valve means as to, in use, cause fluid outflow from said chamber to be at such a rate during a defined measurement time period that said pressure reduces at a constant rate.

3. Equipment according to claim 2, wherein said regulating means is adapted to regulate said valve means in such a manner that said pressure reduces during said measurement time period at a rate of 300 to 500 Pascals per second.

4. Equipment according to claim 2 or 3, wherein said regulating means is operable with a regulating time constant of at least 0.15 seconds.

5. Equipment according to claim 1, comprising means operable under the control of said means responsive to said rate signal to cause onward transmission of Korotkoff tone signals emitted by said microphone to be blocked when said monitored rate represents an increase in the pressure at a rate above said predetermined upper value.

6. Equipment according to claim 1, comprising a first discriminator connected to the output of said microphone for providing output signals indicative of tone signals of the microphone characterising Korotkoff tones, a second discriminator connected to the output of said differentiating means for providing output signals indicative of pressure change signal of the differentiating means characterising heartbeat-induced pressure fluctuations, and tone identifier means connected to the outputs of said first and second discriminators to identify said first discriminator output signals as Korotkoff tone signals when and only when at least the condition is fulfilled that said first and second discriminator output signals occur simultaneously.

7. Equipment according to claim 6, wherein said tone identifier means comprises means operatively connected to said valve means and adapted to so control said valve means as to cause the valve means to fully open when a predetermined minimum period of time has elapsed since identification of a Korotkoff tone signal.

8. Equipment according to claim 6 or 7, comprising means operatively connected to said valve means and adapted to so control said valve means as to cause the valve means to close when the time between last opening of the valve means and first identification of a Korotkoff tone signal is less than a predetermined minimum amount.

9. Equipment according to claim 1, comprising a discriminator connected to output means of said differentiating means and a heartbeat frequency meter having input means connected to output means of said discriminator.

10. A sphygmometer comprising:
an inflatable cuff attachable to a limb;
means including a microphone for detecting sounds generated by blood flow in the limb at the cuff;
pump means for inflating the cuff and thereby tightening same on the limb and restricting blood flow therein;
means including a vent valve connected to the cuff for deflating same;
means including a pressure sensor responsive to fluid pressure in the cuff for generating an output corresponding to the pressure in the cuff;
means including a differentiator connected to the sensor for determining the rate of change in the pressure in the cuff and for generating a rate signal corresponding thereto; and
control means connected to the differentiator and to the vent valve and responsive to the rate signal at least during inflation of the cuff for closing the vent valve when the rate signal exceeds a predetermined limit exceeding a signal level creatable by the blood pressure in the limb to which the cuff is attached.

* * * * *